United States Patent [19]

Saville

[11] Plant 4,642

[45] Feb. 10, 1981

[54] ROSE PLANT

[75] Inventor: Harmon F. Saville, Rowley, Mass.

[73] Assignee: Nor'East Miniature Roses, Inc., Rowley, Mass.

[21] Appl. No.: 109,689

[22] Filed: Jan. 4, 1980

[51] Int. Cl.[3] ..... A01H 5/00

[52] U.S. Cl. ..... Plt./7

[58] Field of Search ..... Plt./7, 9

*Primary Examiner*—Robert E. Bagwill

*Attorney, Agent, or Firm*—Vincent G. Gioia

[57] ABSTRACT

The new peach colored miniature rose which lightens to soft azalea pink tonality upon aging.

1 Drawing Figure

1

The present invention relates to a new and distinct variety of rose plant of the miniature rose class, which was originated by my crossing as seed parent the rose known as "Rise 'N Shine" and the rose known as "Sheri Anne" as pollen parent.

Among the novel characteristics possessed by this new variety which distinguish it from its parents and all other varieties of which I am aware are unusual peach colored flowers borne primarily singly to a stem in a manner typical of hybrid tea plants which lighten upon aging to light peach and then to light pink borne on an upright, compact, uniform branching plant. Asexual reproduction by budding of the new variety as performed in Essex County, Mass., shows that the foregoing and other distinguishing characteristics come true to form and are established and transmitted through succeeding propagations.

The new and improved rose variety which I have developed is an unusual miniature rose in its coloring. Like hybrid teas, the flowers are singly-borne and delightfully displayed against attractive green foliage. The flower color lightens upon aging resulting in an eye-catching plant for display with varying peach and carrot red color tones often visible at the same time.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "37A" is plate 37A of the Royal Horticultural Society Color Chart.

Parentage: Seedling.

*Seed parent.*—"Rise 'N Shine".

*Pollen parent.*—"Sheri Anne".

Class: Miniature.

The following observations are made of specimens grown in Essex County, Mass., during the month of October.

I. FLOWER

Blooming habit: Fast recurrent, near continuous.

A. Bud:

(1) *Size.*—Medium.

2

(2) *Form.*—Ovate.

(3) *Color.*—When sepals first divide and petals begin to unfurl—37A.

(4) *Sepals.*—Foliated, long, thin.

(5) *Peduncle.*—Length—Moderate. Aspect—Straight. Strength—Erect, firm. Color—Near to 139C.

B. Bloom:

(1) *Size.*—Average size when fully expanded—About 1-½ inches.

(2) *Borne.*—Primarily singly.

(3) *Form.*—Relatively high centered at first, becoming flat upon opening.

(4) Petalage.—Number of petals under normal conditions—About 27 to 30.

(5) *Color.*—Bloom begins variously as carrot colored 28B or 28C (also called marigold orange) and lightens to peach or carrot red 29B to 29C as petals unfurl ⅓ to ½ open. Point of attachment of petals show some yellow 14A. Petals also display some center creasing as petals quill. Upon aging, the flower color lightens to light pink 38D. Strong indian yellow colored pollen is significantly visible in open bloom.

C. Petals:

(1) *Texture.*—Firm.

(2) *Appearance.*—Inside—Satiny; Outside—Satiny.

(3) *Form.*—Long, teardrop petals quill and fold under to a point.

(4) *Arrangement.*—Regularly arranged, shingle-like.

(5) *Petaloids in center.*—Few.

(6) *Persistence.*—Drop cleanly.

(7) *Fragrance.*—Slight spicy.

(8) *Lasting quality.*—Average.

2. REPRODUCTIVE ORGANS

A. Stamens, filaments and anthers:

(1) *Arrangement.*—Stamens regularly arranged around styles.

(2) *Color.*—17B.

B. Pollen: Color—17A.

C. Styles: Uneven.

D. Stigmas: Color—47B.

E. Hips: Globular, ⅜-inch diameter, color 168C, seeds do not protrude.

3. PLANT

A. Form: Upright, compact.

B. Growth: Vigorous, uniform branching.

*Height attained.*—12 to 14-inches.

C. Foliage: Compound 5 to 7 leaflet leaves.

(1) *Size.*—Medium.

(2) *Quantity.*—Abundant.

(3) *Color.*—New foliage—Upper side 137b, under side 191B. Old foliage—Upper side 137A, under side 191A.

(4) *Shape.*—Pointed, oval.

(5) *Texture.*—Upper side—Satiny. Under side—Matte.

(6) *Edge.*—Serrated.

(7) *Serration.*—Numerous, fine serrations.

(8) *Leaf stem.*—Color—Near to 139C. Under Side—Near to 139D.

(9) *Stipules.*—Medium length, smooth pointed.

(10) *Resistance to disease.*—Blackspot—Average. Mildew—Average.

D. Wood:

(1) *New wood.*—Color—Near 146D. Bark—Smooth.

(2) *Old wood.*—Color—Near to 144A. Bark—Smooth.

E. Thorns:

(1) *Thorns.*—Quantity—Ordinary. On laterals from stalk—Ordinary. Form—Straight, needle point, slightly downward slant. Length—Long. Color (when young)—185D. Position—Irregular.

(2) *Prickles.*—None.

F. Winter hardiness: Needs some protection in extreme climate.

I claim:

1. A new and distinct variety of rose plant of the miniature class, substantially as shown and described, characterized particularly by peach colored blooms borne primarily singly to a stem on a vigorous plant of attractive foliage which lighten to pale pink upon aging.

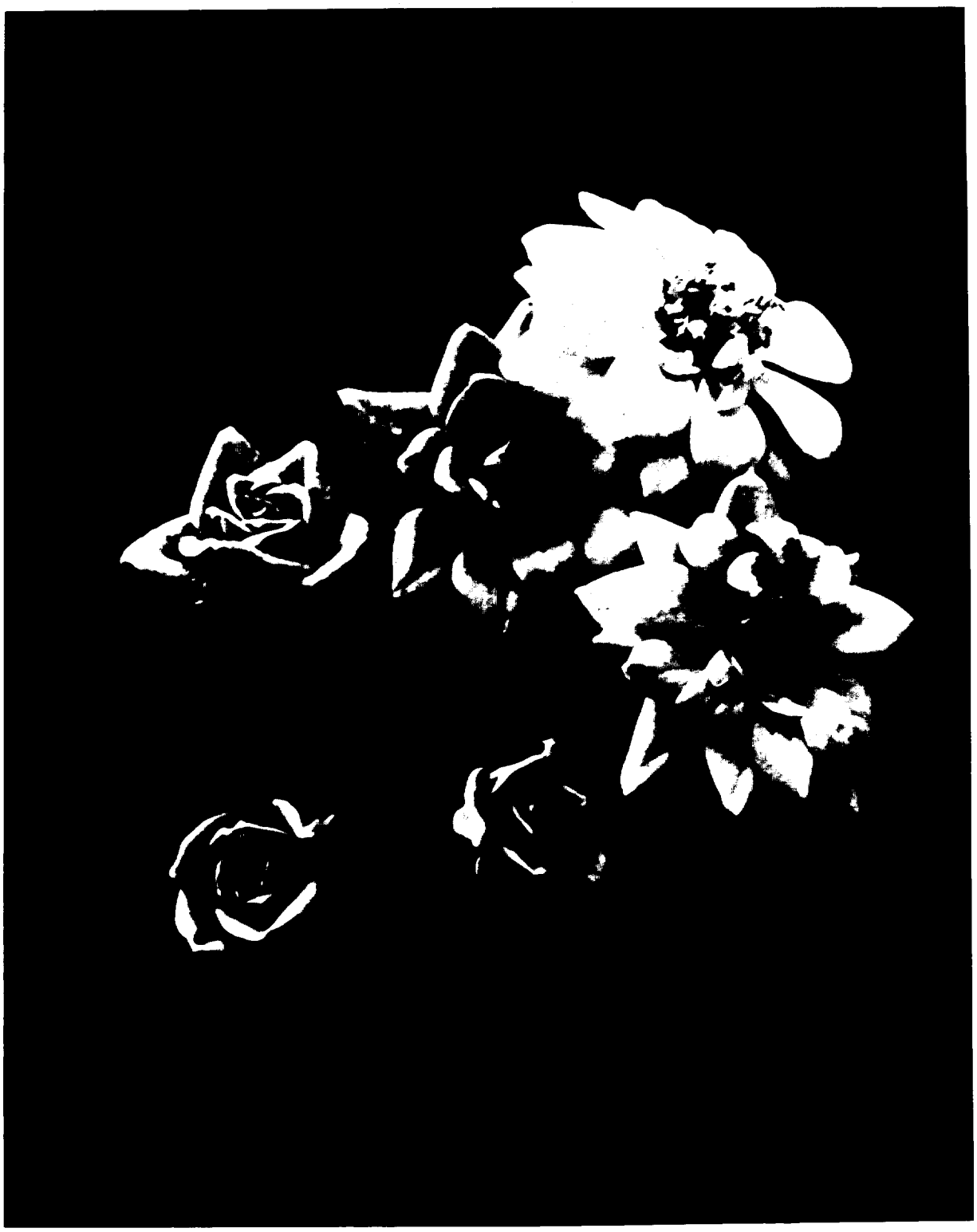

* * * * *